United States Patent [19]
Steinhausen, Jr.

[11] Patent Number: 5,077,779
[45] Date of Patent: Dec. 31, 1991

[54] DENTAL FILM PACKET IMPROVEMENT AND METHOD FOR EFFECTING SAME

[75] Inventor: Theodore B. Steinhausen, Jr., Pittsford, N.Y.

[73] Assignee: Eastman Kodak Company, Rochester, N.Y.

[21] Appl. No.: 645,432

[22] Filed: Jan. 24, 1991

[51] Int. Cl.[5] .......... A61B 6/14
[52] U.S. Cl. .......... 378/168; 378/167; 378/169
[58] Field of Search .......... 378/168, 169, 184

[56] References Cited

U.S. PATENT DOCUMENTS 3,443,093 5/1969 Lindenmuth et al. .......... 250/69
4,831,643 5/1989 Tanaka .......... 378/169
4,912,740 3/1990 Liese, Jr. .......... 378/168
4,922,511 5/1990 Gay .......... 378/168

*Primary Examiner*—Janice A. Howell
*Assistant Examiner*—Kim-Kwok Chu
*Attorney, Agent, or Firm*—William C. Dixon, III

[57] ABSTRACT

A convenience-enhancing improvement upon a known dental film packet (FP) having sensitized film and protective opaque sheets (10 and 12, 14) enclosed by an openable light-tight envelope (16), one of whose opaque sheets (12*c*) covers substantially all of the film sheet (10) when both (12*c* and 10) are partially withdrawn after its envelope (16) has been opened, rendering the film sheet (10) inconvenient to grasp and remove alone. In a first embodiment, the improvement comprises shortening said one opaque sheet (12*c*′) so that it (12*c*′) remains sufficiently protective without covering a graspable end portion (10L′) of the film sheet (10′). In a second (preferred) embodiment, the opaque sheet (12*c*″) is shortened to such an extent that it (12*c*″) covers only an opposite end portion (10*t*″) of the film sheet (10″), and an overlying metal-foil/black-paper laminate (14″) cooperates therewith (12*c*″) to lend further protection but remains inside the envelope (16″), so as not to cover said graspable end portion (10L″), as the film sheet (10″) is withdrawn; this arrangement permits the packet (FP″) to have a thinner and more uniform overall thickness.

10 Claims, 3 Drawing Sheets

DENTAL FILM PACKET IMPROVEMENT AND METHOD FOR EFFECTING SAME

BACKGROUND OF THE INVENTION

1. Field of the Invention

The present invention relates generally to intraoral dental radiographic film packets, and particularly to an improvement therein that renders them more convenient to use.

2. Description of the Prior Art

The prior art is replete with dental film packets of the type referred to above. Examples may be found in the following documents:

U.S. Pat. No. 3,443,093—Discloses a dental x-ray film package comprising sensitized and protective sheets superposed within a readily openable sealed envelope of substantially uniform overall thickness. Dental film packages as described in this patent have been in widespread use for many years. An irksome problem encountered with such packages, however, has been the difficulty experienced in trying to remove only the sensitized sheet from the envelope after that sheet has been radiographically exposed. Such difficulty occurs because that sheet remains completely covered on both sides by the protective sheets when the sensitized and protective sheets are withdrawn together from the opened envelope. All of the sheets are very thin and therefore difficult to separate, especially when working entirely by feel in the dark. Although various attempts to resolve that problem have been made over the years, none has yet proven fully satisfactory.

U.S. Pat. No. 4,831,643—Discloses a dental x-ray film pack embodying one such attempt, wherein protective opaque and reflecting components superposed upon part of a sensitized film sheet are adhesively bonded to an overlying peelable flap portion of an enclosing envelope, in order to be automatically removed from the film sheet when the flap portion is peeled away to open the envelope. Although the thus-uncovered part of the film sheet is thereby rendered accessible for grasping by the user, such a scheme is complex and costly to manufacture, it makes the envelope flap portion stiffer and more resistant to being peeled away when the envelope is to be opened, and its reliability is dependent upon the integrity of its adhesive bonds.

There has thus remained a need for a solution to the above-described problem that is simple, efficient, and economical to adopt, and which is highly reliable, practical, and convenient when in use.

SUMMARY OF THE INVENTION

The primary object of this invention has been to meet the foregoing need. That object and others have been achieved by the invention herein disclosed and claimed.

This invention finds utility as a convenience-enhancing improvement upon a known intraoral dental radiographic film packet of the type having a sensitized film sheet including leading and trailing end portions and an intermediate portion between the end portions; a foldable opaque sheet including a bottom section underlying the film sheet, a top section folded around the trailing end portion of the film sheet and overlying substantially all of the film sheet, and a tab section folded around the leading end portion of the film sheet and overlying both that leading end portion and a forward part of the top section of the opaque sheet; a reflective sheet including main and front-end portions overlying the top section of the opaque sheet, with the front-end portion interposed between the forward part of the top section and the tab section of the opaque sheet; and an opaque envelope for protectively enclosing the film sheet, the opaque sheet, and the reflective sheet, the envelope including a bottom wall underlying the bottom section of the opaque sheet, a top-wall cover section overlying the main portion of the reflective sheet and including a forward portion extending forwardly toward the tab section of the opaque sheet, and a top-wall flap section overlying the tab section of the opaque sheet and including a tab portion thereof projecting rearwardly over the forward portion of the top-wall cover section, the bottom wall and the top-wall cover and flap sections of the envelope being separably joined together along facing marginal portions thereof surrounding the sheets to make the envelope light-tight, the top-wall flap section being readily separable from the top-wall cover section and the bottom wall, by pulling upon the tab portion of the flap section, to open the envelope for removal of the film sheet after radiographic exposure thereof.

The claimed convenience-enhancing improvement to such a packet comprises: a shortened top section of the opaque sheet, the top section being so shortened as to overlie at least the trailing end portion of the film sheet but not more than the trailing end portion plus the intermediate portion of the film sheet; a tab section of the opaque sheet of such length as to overlie at least the leading end portion of the film sheet but no part of the shortened top section; and a reflective sheet whose main portion overlies the shortened top section and whose front-end portion is interposed between the tab section of the opaque sheet and the leading end portion of the film sheet; the opaque sheet and the film sheet together being freely slidable, relative to and outwardly away from both the reflective sheet and the envelope, in response to forward pulling upon the tab section of the opaque sheet after the envelope has been opened; and the tab section of the opaque sheet being readily unfolded away from the leading end portion of the film sheet thereunder, in response to the forward pulling upon the tab section, to uncover the leading end portion and thus enable convenient grasping thereof to remove only the film sheet from the envelope for processing.

This invention, and its objects and advantages, will become more apparent in the detailed description of its illustrated embodiments presented hereinbelow.

BRIEF DESCRIPTION OF THE DRAWINGS

In the detailed description of the two embodiments of this invention presented below, reference is made to the accompanying drawings, wherein like reference characters denote like elements, and wherein.

DESCRIPTION OF THE ILLUSTRATED EMBODIMENTS

Figure 1:
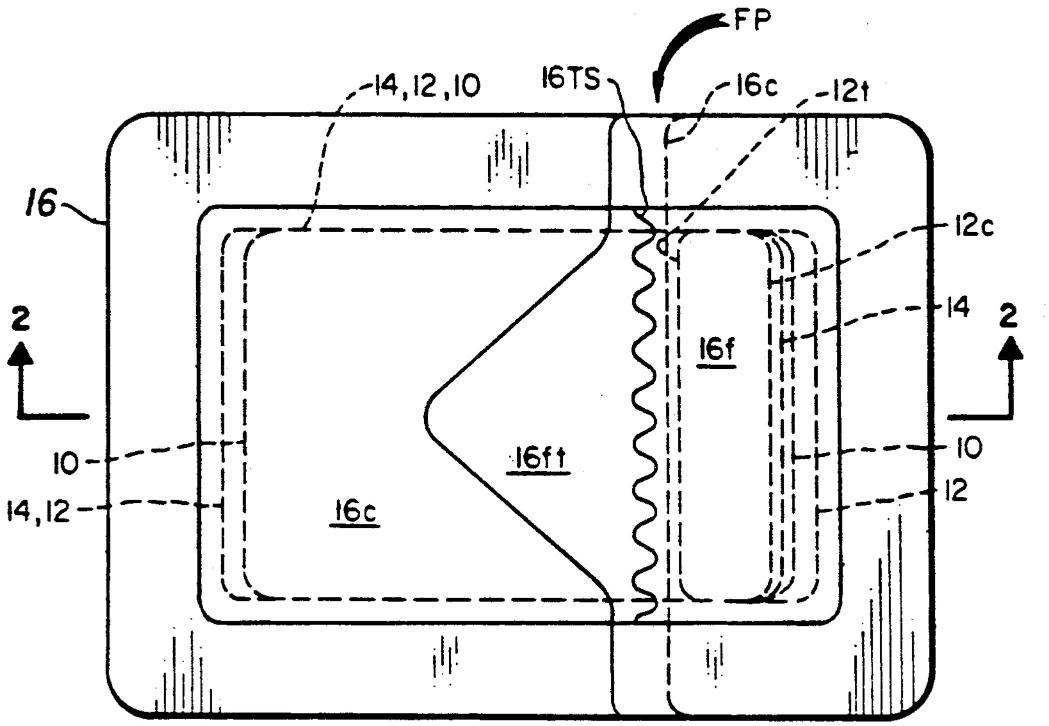
FIG. 1 (PRIOR ART)
FIG. 1 is a top-plan view of an intraoral dental radiographic film packet as known in the prior art, and to which the film packet improvement of this invention is directed.

Because certain parts of intraoral dental radiographic film packets are well known, the following description is directed in particular to those elements forming, cooperating directly with, or relating to, this invention. Elements not specifically shown or described herein are selectable from those known in the relevant art.

FIGS. 1–4 illustrate an intraoral dental radiographic film packet of a type known in the prior art, e.g., as disclosed in the aforementioned U.S. Pat. No. 3,443,093, and to which the film packet improvement of this invention is directed. The known packet, designated generally by the letters FP, comprises a sheet of x-ray film 10 that includes leading and trailing end portions 10L and 10t, respectively, and an intermediate portion 10i between those end portions, film sheet 10 having a sensitive emulsion on one or both sides (as is well known in the art); a folded, opaque, black-paper wrapper 12; a sheet of reflective metal foil 14 of substantially the same shape and size as the film sheet 10; and an opaque enclosing envelope 16, preferably plastic, within which the foregoing components are arranged as shown and sealed. As is well known, the envelope 16 may be made of a duplex plastic sheet, i.e., a sheet of white plastic on the outside laminated to a sheet of black plastic on the inside. The plastic preferred for the envelope is polyvinylchloride, although polyethylene, Pliofilm, cryovac, or other plastic films or combinations of plastics might also be used. The white outside surface of the envelope may be matte, glossy, or embossed. The metal foil sheet 14 preferably is made of lead, but any metal that absorbs x-rays satisfactorily for dental radiographic purposes may be employed.

Figure 2:
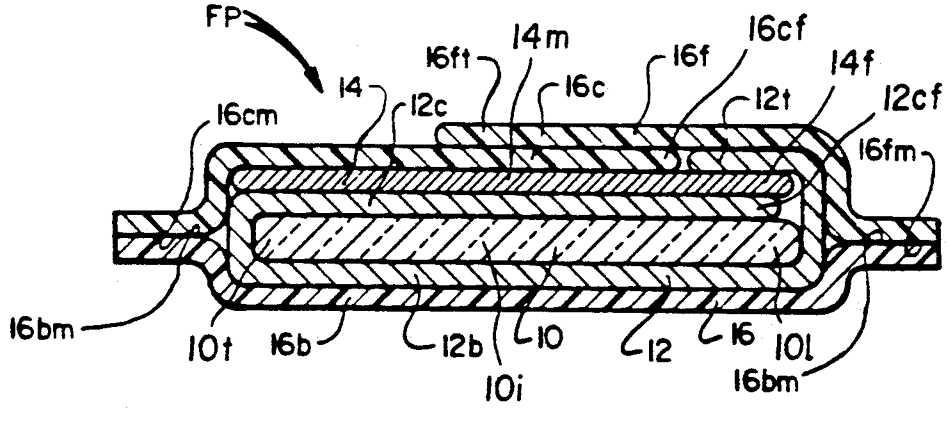
FIG. 2 (PRIOR ART)
FIG. 2 is a cross-sectional elevation of the known packet depicted in FIG. 1, taken along line 2—2 therein and showing principal components thereof exaggerated in thickness for clarity of illustration.
Figure 3:
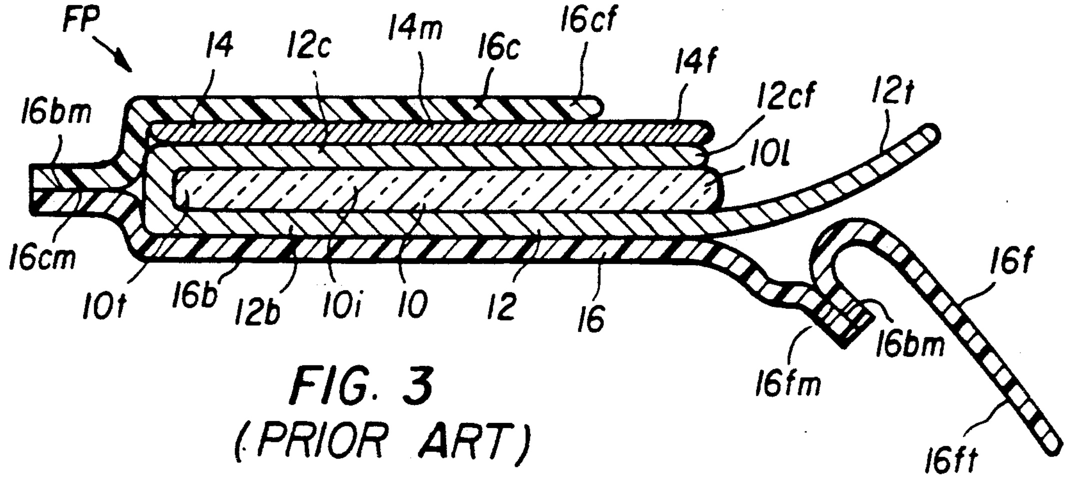
FIG. 3 (PRIOR ART)
FIG. 3 also is a cross-sectional elevation of the known packet depicted in FIG. 1, similar to FIG. 2 but illustrating the packet therein after its envelope has been opened and its opaque sheet tab section unfolded from the leading end portion of the film sheet.

In the assembled prior-art film packet, as shown in FIG. 2, the opaque black-paper wrapper 12 comprises a base or bottom section **12*b* underlying film sheet 10, a folded-over cover or top section 12*c* overlying film sheet 10, and a folded-over tab section 12*t* overlying the right-hand end portions 10L and 12*cf*, respectively, of film sheet 10 and cover section 12*c*. It will be seen that the reflective metal foil sheet 14 lies between the cover or top section 12*c* and tab section 12*t*, sheet 14 having main and front-end portions 14*m* and 14*f*, respectively, that overlie top section 12*c*, with the front-end portion 14*f* interposed between the right-end or forward portion 12*cf* of section 12*c* and tab section 12*t*. The plastic envelope 16 comprises a bottom wall 16*b* underlying the paper wrapper base or bottom section 12*b*, a top-wall cover section 16*c* overlying the main portion 14*m* of metal foil sheet 14 and having a forward portion 16*cf* extending forwardly toward the wrapper tab section 12*t*, and a top-wall flap section 16*f* overlying both the wrapper tab section 12*t* and the envelope cover section 16*c*. Cover section 16*c* and flap section 16*f* together form the top wall of the envelope. As shown in FIG. 1, the left-hand end portion of envelope flap section 16*f* is triangular in shape, to form a tab end 16*ft* of the flap section that projects rearwardly over the cover section forward portion 16*cf*. Flap section 16*f* is tack-sealed to cover section 16*c* transversely of the envelope, as indicated by the undulated line 16TS. The envelope bottom wall 16*b* includes an upward-facing marginal area 16*bm* which is sealed to an opposing downward-facing marginal area 16*cm* of cover section 16*c* and an opposing downward-facing marginal area 16*fm* of flap section 16*f*. The seal may be provided in any suitable manner, e.g., by heat, ultrasonics, or an adhesive. To open the packet for processing film sheet 10 after its exposure, the technician first grasps the unsealed tab end 16*ft* of flap section 16*f* and then pulls the flap section upwardly, so as to break the transverse seal 16TS and rip open the seal between marginal areas 16*fm* and 16*bm*. With the envelope thus opened, the technician then grasps and unfolds the wrapper tab section 12*t*, as shown in FIG. 3, and then pulls wrapper 12 out of the envelope with film sheet 10 riding between the wrapper base and cover sections 12*b* and 12*c***, as depicted in FIG. 4.

Figure 4:
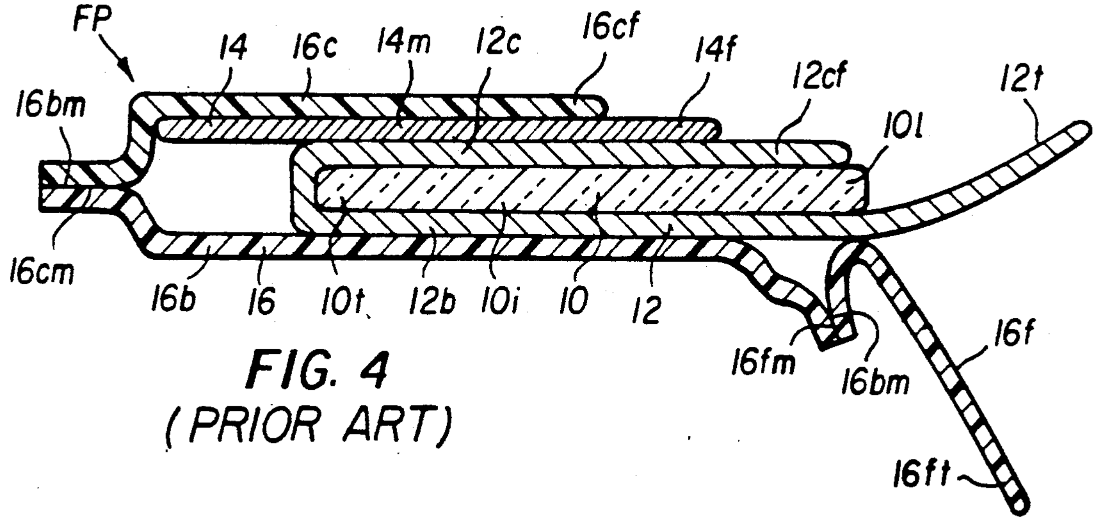
FIG. 4 (PRIOR ART)
FIG. 4 also is a cross-sectional elevation of the known packet of FIG. 1, similar to FIG. 3 but showing the packet therein after its opaque sheet and film sheet have been partially withdrawn from the envelope.

With particular reference to FIG. 4, showing the prior-art film packet FP after its envelope 16 has been opened, its wrapper tab section **12*t* unfolded, and its wrapper 12 and film sheet 10 partially withdrawn, it will be seen that the right-hand or leading end portion 10L of film sheet 10 is covered by the right-hand or forward portion 12*cf* of wrapper cover section 12*c***, making it difficult for the technician to separate the film sheet from its wrapper and remove only the film sheet for processing. That difficulty has now been overcome by this invention, as exemplified by the two embodiments thereof illustrated in FIGS. 5–8.

THE FIRST EMBODIMENT

Figure 5:
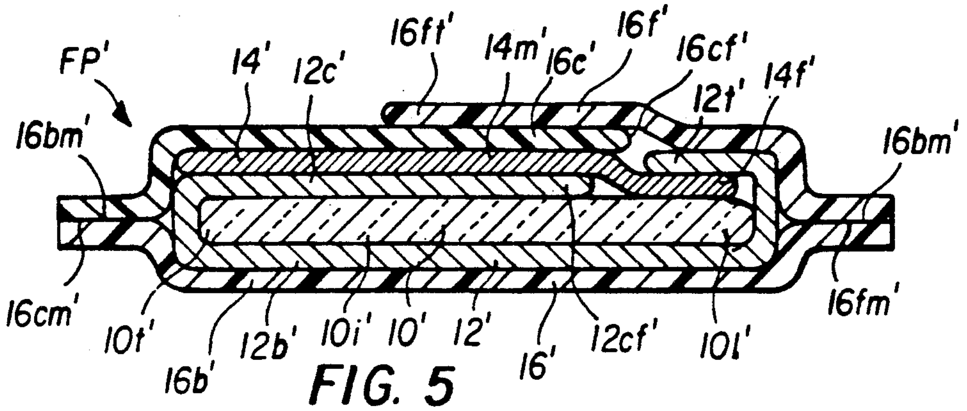
FIG. 5 is a cross-sectional elevation similar to FIG. 2 but depicting the packet therein as improved by a first embodiment of this invention, and as disposed in its normally closed condition.
Figure 6:
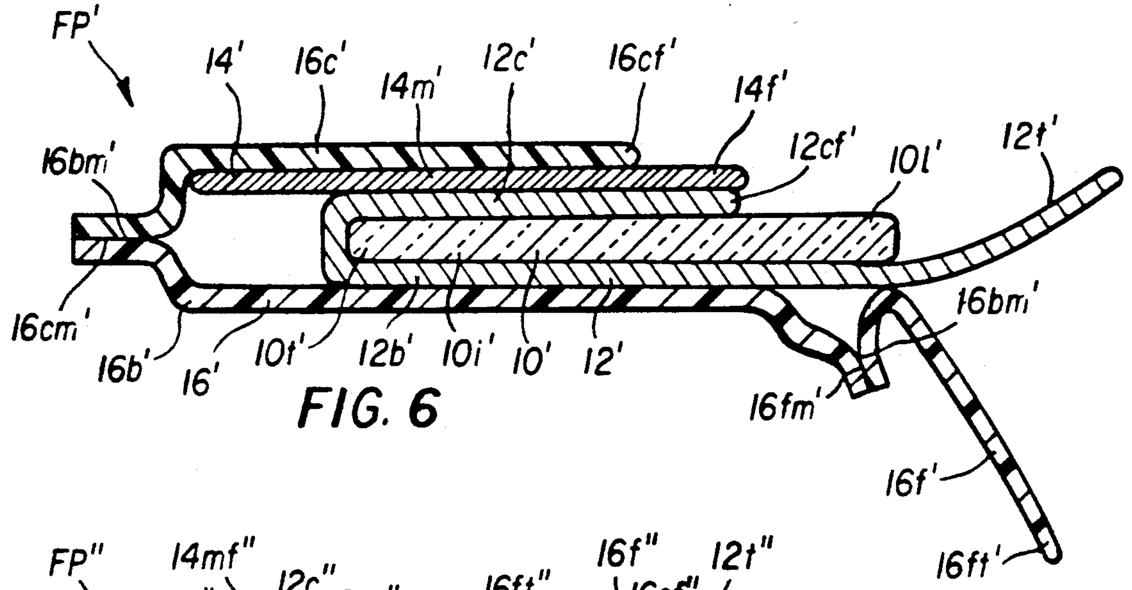
FIG. 6 is a cross-sectional elevation of the improved packet shown in FIG. 5, illustrating that packet after its envelope has been opened, its opaque sheet tab section unfolded, and its opaque sheet and film sheet partially withdrawn from the envelope.

The first embodiment is depicted in FIGS. 5 and 6, wherein elements corresponding to those shown in FIGS. 1–4 are designated by the same reference characters primed. FIG. 5 thus shows a dental film packet FP′ having a sensitized film sheet 10′ including leading and trailing end portions 10L′ and **10*t*′ and an intermediate portion 10*i*′ therebetween. Packet FP′ has a foldable, opaque, black-paper wrapper sheet 12′ including a bottom section 12*b*′ underlying film sheet 10′, a shortened top section 12*c*′ folded around the film sheet trailing end portion 10*t*′ and overlying both the trailing end portion 10*t*′ and a substantial part of intermediate portion 10*i*′, its forward part 12*cf* extending not beyond intermediate portion 10*i*′, and a tab section 12*t*′ folded around the film sheet leading end portion 10L′ and overlying at least the leading end portion 10L′ but no part of the shortened top section 12*c*′. Packet FP′ also has a reflective metal-foil sheet 14′, preferably of lead, including a main portion 14*m*′ that overlies the shortened top section 12*c*′ and a front-end portion 14*f*′ interposed between the opaque sheet tab section 12*t*′ and the film sheet leading end portion 10L'. Packet FP' finally has a protective, opaque, thermoplastic envelope 16', preferably of polyvinylchloride, including a bottom wall 16b' that underlies the opaque sheet bottom section 12b', a top-wall cover section 16c' that overlies the reflective sheet main portion 14m' and has a forward portion 16cf extending forwardly (to the right, as viewed in FIG. 5) toward the opaque sheet tab section 12t', and a top-wall flap section 16f' that overlies the opaque sheet tab section 12t' and has a tab portion 16ft' projecting rearwardly (to the left, as viewed in FIG. 5) over the top-wall cover section forward portion 16cf. As in the prior-art film packet described above with reference to FIGS. 1–4, the top-wall flap section 16f' is tack-sealed to the top-wall cover section 16c' transversely of the envelope, both sections 16f' and 16c' together forming the envelope top wall. The envelope bottom wall 16b' includes an upward-facing marginal area 16bm' that is sealed to an opposing downward-facing marginal area 16cm' of cover section 16c' and to an opposing downward-facing marginal area 16fm' of flap section 16f', to render envelope 16' light-tight. Flap section 16f' is readily separable from cover section 16c' and bottom wall 16b' to open envelope 16', in the same manner as described above with reference to the packet of FIGS. 1–4. The opaque sheet 12' and film sheet 10' together are freely slidable, relative to and outwardly (to the right, as viewed in FIG. 5) away from both the reflective sheet 14' and envelope 16', in response to forward (to the right) pulling upon tab section 12t' after the envelope has been opened. During such pulling, tab section 12t' is readily unfolded (clockwise as viewed in FIG. 5) away from the film sheet leading end portion 10L', to uncover said leading end portion and thereby enable convenient grasping thereof to remove only the film sheet from the envelope, all as shown in FIG. 6**.

THE SECOND (PREFERRED) EMBODIMENT

Figure 7:
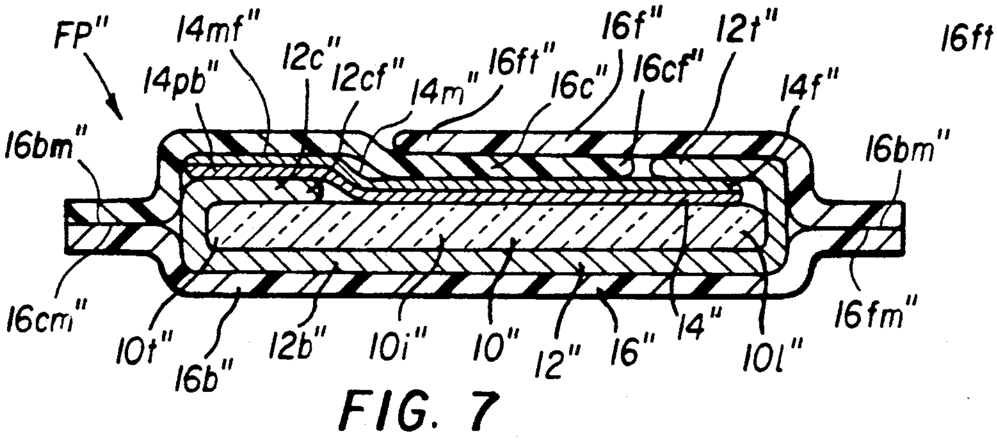
FIG. 7 also is a cross-sectional elevation similar to FIG. 2 but depicting the packet therein as improved by a second (the preferred) embodiment of this invention, and as disposed in its normally closed condition.
Figure 8:
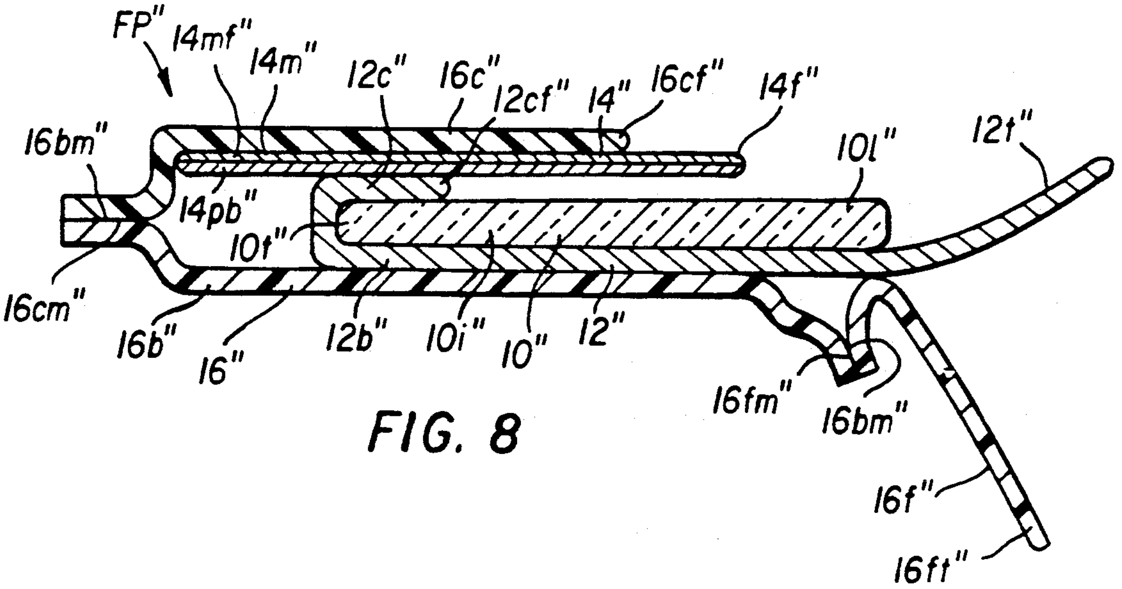
FIG. 8 is a cross-sectional elevation of the improved packet shown in FIG. 7, illustrating that packet after its envelope has been opened, its opaque sheet tab section unfolded, and its opaque sheet and film sheet partially withdrawn from the envelope.

The second (preferred) embodiment is depicted in FIGS. 7 and 8, wherein elements corresponding to those shown in FIGS. 1–4 are designated by the same reference characters double-primed. FIG. 7 thus shows a dental film packet FP" having a sensitized film sheet 10" including leading and trailing end portions 10L" and 10t" and an intermediate portion 10i" therebetween. Packet FP" has a foldable, opaque, black-paper wrapper sheet 12" including a bottom section 12b" underlying film sheet 10", a more-shortened top section 12c" folded around the film sheet trailing end portion 10t" and overlying the trailing end portion 10t" only, its forward part 12cf" extending toward but not over intermediate portion 10i", and a tab section 12t" folded around the film sheet leading end portion 10L" and overlying the leading end portion 10L" only, its free end extending toward but not over intermediate portion 10i". Packet FP" also has a reflective sheet 14" comprising a metal foil 14mf", preferably lead, that is laminated to a black-paper backing 14pb". The laminated reflective sheet 14" includes a main portion 14m", which overlies both the opaque sheet shortened top section 12c" and the film sheet intermediate portion 10i", and a front-end portion 14f" that is interposed between the opaque sheet tab section 12t" and the film sheet leading end portion 10L". Packet FP" finally has a protective, opaque, thermoplastic envelope 16", preferably of polyvinylchloride, including a bottom wall 16b" that underlies the opaque sheet bottom section 12b", a top-wall cover section 16c" that overlies the reflective sheet main portion 14m" and has a forward portion 16cf" extending forwardly (to the right, as viewed in FIG. 7) toward the opaque sheet tab section 12t", and a top-wall flap section 16f" that overlies the opaque sheet tab section 12t" and has a tab portion 16ft" projecting rearwardly (to the left, as viewed in FIG. 7) over the top-wall cover section forward portion 16cf". Inside envelope 16", the laminated reflective sheet 14" is oriented so that its metal foil 14mf" faces both the envelope top-wall cover section 16c" and the opaque sheet tab section 12t", and its black-paper backing 14pb" faces both the opaque sheet shortened top section 12c" and the film sheet intermediate and leading end portions 10i" and 10L". As in the prior-art film packet discribed above with reference to FIGS. 1–4, the top-wall flap section 16f" is tack-sealed to the top-wall cover section 16c" transversely of the envelope, both sections 16f" and 16c" together forming the envelope top wall. The envelope bottom wall 16b" includes an upward-facing marginal area 16bm" that is sealed to an opposing downward-facing marginal area 16cm" of cover section 16c" and to an opposing downward-facing marginal area 16fm" of flap section 16f", to render envelope 16" light-tight. Flap section 16f" is readily separable from cover section 16c" and bottom wall 16b" to open envelope 16", in the same manner as described above with reference to the packet of FIGS. 1–4. The opaque sheet 12" and film sheet 10" together are freely slidable, relative to and outwardly (to the right, as viewed in FIG. 7) away from both the reflective sheet 14" and envelope 16", in response to forward (to the right) pulling upon tab section 12t" after the envelope has been opened. During such pulling, tab section 12t" *is readily unfolded (clockwise as viewed in FIG. 7) away from the film sheet leading end portion 10L", to uncover said leading end portion and thereby enable convenient grasping thereof to remove only the film sheet from the envelope, all as shown in FIG. 8.*

The second embodiment is preferred over the first embodiment because its use of a metal-foil/black-paper laminate, instead of a metal foil only, provides greater light-locking protection and thereby permits use of a shorter opaque sheet top section without jeopardizing the packet's light-locking integrity. Also, as may be seen by comparing FIGS. 5 and 7, the second embodiment allows the packet to have a thinner and more uniform overall thickness. Both embodiments effectively overcome the aforementioned problem left unsolved by the prior art, in a way that is simple, efficient, and economical to adopt, and reliable, practical, and convenient to use.

Although the present invention has now been described in detail with particular reference to its two embodiments illustrated herein, it will be understood that further variations and modifications can still be effected within the scope of this invention as set forth in the following claims.

I claim:

1. A convenience-enhancing improvement upon an intraoral dental radiographic film packet (FP) of the type having a sensitized film sheet (10) including leading and trailing end portions thereof (10L and 10t) and an intermediate portion (10i) between said end portions (10L and 10t); a foldable opaque sheet (12) including a bottom section thereof (12b) underlying the film sheet (10), a top section thereof (12c) folded around said trailing end portion (10t) of the film sheet (10) and overlying substantially all of the film sheet (10), and a tab section thereof (12*t*) folded around said leading end portion (10L) of the film sheet (10) and overlying both said leading end portion (10L) and a forward part (12*cf*) of said top section (12*c*) of the opaque sheet (12); a reflective sheet (14) including main and front-end portions thereof (14*m* and 14*f*) overlying said top section (12*c*) of the opaque sheet (12), with said front-end portion thereof (14*f*) interposed between said forward part (12*cf*) of said top section (12*c*) and said tab section (12*t*) of the opaque sheet (12); and an opaque envelope (16) for protectively enclosing the film sheet (10), the opaque sheet (12), and the reflective sheet (14), the envelope (16) including a bottom wall (16*b*) underlying said bottom section (12*b*) of the opaque sheet (12), a top-wall cover section (16*c*) overlying said main portion (14*m*) of the reflective sheet (14) and including a forward portion thereof (16*cf*) extending forwardly toward said tab section (12*t*) of the opaque sheet (12), and a top-wall flap section (16*f*) overlying said tab section (12*t*) of the opaque sheet (12) and including a tab portion thereof (16*ft*) projecting rearwardly over said forward portion (16*cf*) of said top-wall cover section (16*c*), said bottom wall (16*b*) and said top-wall cover and flap sections (16*c* and 16*f*) of the envelope (16) being separably joined together along facing marginal portions thereof (16*bm*–16*cm* and 16*bm*–16*fm*) surrounding the sheets (10, 12, and 14) to make said envelope (16) light-tight, said top-wall flap section (16*f*) being readily separable from said top-wall cover section (16*c*) and said bottom wall (16*b*), by pulling upon said tab portion (16*ft*) of said flap section (16*f*), to open the envelope (16) for removal of the film sheet (10) after radiographic exposure thereof (10); said convenience-enhancing improvement comprising:

- a shortened top section (12*c*′ or 12*c*″) of the opaque sheet (12′ or 12″), said top section (12*c*′ or 12*c*″) being so shortened as to overlie at least said trailing end portion (10*t*′ or 10*t*″) of the film sheet (10′ or 10″) but not more than said trailing end portion (10*t*′ or 10*t*″) plus said intermediate portion (10*i*′ or 10*i*″) of the film sheet (10′ or 10″);
- a tab section (12*t*′ or 12*t*″) of the opaque sheet (12′ or 12″) of such length as to overlie at least said leading end portion (10L′ or 10L″) of the film sheet (10′ or 10″) but no part of said shortened top section (12*c*′ or 12*c*″); and
- a reflective sheet (14′ or 14″) whose main portion (14*m*′ or 14*m*″) overlies said shortened top section (12*c*′ or 12*c*″) and whose front-end portion (14*f*′ or 14*f*″) is interposed between said tab section (12*t*′ or 12*t*″) of the opaque sheet (12′ or 12″) and said leading end portion (10L′ or 10L″) of the film sheet (10′ or 10″);
- the opaque sheet (12′ or 12″) and the film sheet (10′ or 10″) together being freely slidable, relative to and outwardly away from both the reflective sheet (14′ or 14″) and the envelope (16′ or 16″), in response to forward pulling upon said tab section (12*t*′ or 12*t*″) of the opaque sheet (12′ or 12″) after the envelope (16′ or 16″) has been opened; and
- said tab section (12*t*′ or 12*t*″) of the opaque sheet (12′ or 12″) being readily unfolded away from said leading end portion (10L′ or 10L″) of the film sheet thereunder (10′ or 10″), in response to said forward pulling upon said tab section (12*t*′ or 12*t*″), to uncover said leading end portion (10L′ or 10L″) and thus enable convenient grasping thereof (10L′ or 10L″) to remove the film sheet only (10′ or 10″) from the envelope (16′ or 16″) for processing.

2. A convenience-enhancing improvement as claimed in claim 1 wherein said shortened top section (12*c*″) of the opaque sheet (12″) overlies only said trailing end portion (10*t*″) of the film sheet (10″), wherein said tab section (12*t*″) of the opaque sheet (12″) overlies only said leading end portion (10L″) of the film sheet (10″), and wherein said main portion (14*m*″) of the reflective sheet (14″) overlies both said shortened top section (12*c*″) of the opaque sheet (12″) and said intermediate portion (10*i*″) of the film sheet (10″).

3. A convenience-enhancing improvement as claimed in claim 2 wherein the opaque sheet (12″) comprises a black paper, wherein the reflective sheet (14″) comprises a metal foil (14*mf*″), and wherein the envelope (16″) comprises a thermoplastic material.

4. A convenience-enhancing improvement as claimed in claim 3 wherein said metal foil (14*mf*″) is laminated to a black-paper backing (14*pb*″), wherein said foil (14*mf*″) faces said top-wall cover section (16*c*″) of the envelope (16″) and said tab section (12*t*″) of the opaque sheet (12″), and wherein said backing (14*pb*″) faces said shortened top section (12*c*″) of the opaque sheet (12″) and said intermediate and leading end portions (10*i*″ and 10L″) of the film sheet (10″).

5. A convenience-enhancing improvement as claimed in claim 4 wherein said metal foil (14*mf*″) includes lead, and wherein said thermoplastic material includes polyvinylchloride.

6. A method for rendering an intraoral dental radiographic film packet (FP) more convenient to use, the packet (FP) having a sensitized film sheet (10) including leading and trailing end portions thereof (10L and 10*t*) and an intermediate portion (10*i*) between said end portions (10L and 10*t*); a foldable opaque sheet (12) including a bottom section thereof (12*b*) underlying the film sheet (10), a top section thereof (12*c*) folded around said trailing end portion (10*t*) of the film sheet (10) and overlying substantially all of the film sheet (10), and a tab section thereof (12*t*) folded around said leading end portion (10L) of the film sheet (10) and overlying both said leading end portion (10L) and a forward part (12*cf*) of said top section (12*c*) of the opaque sheet (12); a reflective sheet (14) including main and front-end portions thereof (14*m* and 14*f*) overlying said top section (12*c*) of the opaque sheet (12), with said front-end portion thereof (14*f*) interposed between said forward part (12*cf*) of said top section (12*c*) and said tab section (12*t*) of the opaque sheet (12); and an opaque envelope (16) for protectively enclosing the film sheet (10), the opaque sheet (12), and the reflective sheet (14), the envelope (16) including a bottom wall (16*b*) underlying said bottom section (12*b*) of the opaque sheet (12), a top-wall cover section (16*c*) overlying said main portion (14*m*) of the reflective sheet (14) and including a forward portion thereof (16*cf*) extending forwardly toward said tab section (12*t*) of the opaque sheet (12), and a top-wall flap section (16*f*) overlying said tab section (12*t*) of the opaque sheet (12) and including a tab portion thereof (16*ft*) projecting rearwardly over said forward portion (16*cf*) of said top-wall cover section (16*c*), said bottom wall (16*b*) and said top-wall cover and flap sections (16*c* and 16*f*) of the envelope (16) being separably joined together along facing marginal portions thereof (16*bm*–16*cm* and 16*bm*–16*fm*) surrounding the sheets (10, 12, and 14) to make said envelope (16) light-tight, said top-wall flap section (16*f*)

being readily separable from said top-wall cover section (16c) and said bottom wall (16b), by pulling upon said tab portion (16ft) of said flap section (16f), to open the envelope (16) for removal of the film sheet (10) after radiographic exposure thereof (10); said method comprising:

- limiting said top section (12c' or 12c'') of the opaque sheet (12' or 12'') in length such that said top section (12c' or 12c'') overlies at least said trailing end portion (10t' or 10t'') of the film sheet (10' or 10'') and at most said trailing end portion (10t' or 10t'') plus said intermediate portion (10i' or 10i'') of the film sheet (10' or 10'');
- limiting said tab section (12t' or 12t'') of the opaque sheet (12' or 12'') in length such that said tab section (12t' or 12t'') overlies at least said leading end portion (10L' or 10L'') of the film sheet (10' or 10'') but no part of said top section (12c' or 12c'');
- arranging the reflective sheet (14' or 14'') so that its main portion (14m' or 14m'') overlies said top section (12c' or 12c'') of the opaque sheet 12' or 12'') while its front-end portion (14f' or 14f'') is interposed between said tab section (12t' or 12t'') of the opaque sheet (12' or 12'') and said leading end portion (10L' or 10L'') of the film sheet (10' or 10'');
- allowing the opaque sheet (12' or 12'') and the film sheet (10' or 10'') to be freely slidable together, relative to and outwardly away from both the reflective sheet (14' or 14'') and the envelope (16' or 16''), in response to forward pulling upon said tab section (12t' or 12t'') of the opaque sheet (12' or 12'') after the envelope (16' or 16'') has been opened; and
- allowing said tab section (12t' or 12t'') of the opaque sheet (12' or 12'') to be readily unfolded away from said leading end portion (10L' or 10L'') of the film sheet thereunder (10' or 10''), in response to said forward pulling upon said tab section (12t' or 12t''), to uncover said leading end portion (10L' or 10L'') and thus enable convenient grasping thereof (10L' or 10L'') to remove the film sheet only (10' or 10'') from the envelope (16' or 16'') for processing.

7. A method as claimed in claim 6 wherein said limiting said top section (12c' or 12c'') of the opaque sheet (12' or 12'') in length is such that said top section (12c'') overlies only said trailing end portion (10t'') of the film sheet (10''), wherein said limiting said tab section (12t' or 12t'') of the opaque sheet 12' or 12'') in length is such that said tab section (12t'') overlies only said leading end portion (10L'') of the film sheet (10''), and wherein said arranging the reflective sheet (14' or 14'') is such that its main portion (14m'') overlies both said top section (12c'') of the opaque sheet (12'') and said intermediate portion (10i'') of the film sheet (10'').

8. A method as claimed in claim 7 further comprising forming the opaque sheet (12'') from a foldable black paper, forming the reflective sheet (14'') from a metal foil (14mf''), and forming the envelope (16'') from a thermoplastic material.

9. A method as claimed in claim 8 further comprising laminating said metal foil (14mf'') to a black-paper backing (14pb'') to form a metal-foil/black-paper laminate (14''), and arranging the laminate (14'') so that said foil (14mf'') faces said top-wall cover section (16c'') of the envelope (16'') and said tab section (12t'') of the opaque sheet (12'') while said backing (14pb'') faces said top section (12c'') of the opaque sheet (12'') and said intermediate and leading end portions (10i'' and 10L'') of the film sheet (10'').

10. A method as claimed in claim 9 wherein said metal foil (14mf'') includes lead, and said thermoplastic material includes polyvinylchloride.

* * * * *